(12) United States Patent
Beck et al.

(10) Patent No.: US 10,624,378 B2
(45) Date of Patent: Apr. 21, 2020

(54) PROCESS OF PRODUCTION OF A FORMULATION COMPRISING THERAPEUTICALLY ACTIVE OR NUTRITIOUS PLANT EXTRACTS

(71) Applicant: DSM IP Assets B.V., Heerlen (NL)

(72) Inventors: Markus Beck, Kaiseraugst (CH);
Andrea Bulbarello, Kaiseraugst (CH);
Kevin Prudence, Kaiseraugst (CH);
Loni Schweikert, Kaiseraugst (CH);
Kai Urban, Kaiseraugst (CH)

(73) Assignee: DSM IP ASSETS B.V., Heerlen (NL)

( * ) Notice: Subject to any disclaimer, the term of this patent is extended or adjusted under 35 U.S.C. 154(b) by 0 days.

(21) Appl. No.: 15/756,626

(22) PCT Filed: Sep. 9, 2016

(86) PCT No.: PCT/EP2016/071320
§ 371 (c)(1),
(2) Date: Mar. 1, 2018

(87) PCT Pub. No.: WO2017/042340
PCT Pub. Date: Mar. 16, 2017

(65) Prior Publication Data
US 2018/0352842 A1 Dec. 13, 2018

(30) Foreign Application Priority Data

Sep. 9, 2015 (EP) .................................... 15184393

(51) Int. Cl.
| | |
|---|---|
| A61K 36/185 | (2006.01) |
| A23L 33/105 | (2016.01) |
| A61K 9/16 | (2006.01) |
| A23L 5/00 | (2016.01) |
| A23L 27/00 | (2016.01) |
| A61K 36/736 | (2006.01) |
| A23P 10/40 | (2016.01) |

(52) U.S. Cl.
CPC ............... *A23L 33/105* (2016.08); *A23L 5/00* (2016.08); *A23L 27/70* (2016.08); *A23L 27/84* (2016.08); *A23P 10/40* (2016.08); *A61K 9/1617* (2013.01); *A61K 36/185* (2013.01); *A61K 36/736* (2013.01); *A23V 2002/00* (2013.01); *A61K 2236/00* (2013.01)

(58) Field of Classification Search
CPC ..................................................... A61K 36/185
See application file for complete search history.

(56) References Cited

U.S. PATENT DOCUMENTS

| | | |
|---|---|---|
| 2002/0182269 A1 | 12/2002 | Dreyer et al. |
| 2003/0203052 A1 | 10/2003 | Dreyer et al. |
| 2015/0105338 A1 | 4/2015 | O'Kennedy |

FOREIGN PATENT DOCUMENTS

| | | |
|---|---|---|
| CN | 103491801 | 1/2014 |
| JP | 2002-029968 | 1/2002 |
| KR | 10-2012-0081788 | 7/2012 |
| WO | WO 2012/143492 | 10/2012 |

OTHER PUBLICATIONS

Wijngaard et al.,"Techniques to extract bioactive compounds from food by-products of plant origin," Food Research International 46: 505-513, 2012.*
International Search Report for PCT/EP2016/071320, dated Nov. 7, 2016, 4 pages.
Official Action, CN Appin. 201680051616.9, Dec. 17, 2019.

* cited by examiner

*Primary Examiner* — Rosanne Kosson
(74) *Attorney, Agent, or Firm* — Nixon & Vanderhye P.C.

(57) ABSTRACT

This invention relates to a process for producing solid formulations. These solid formulations comprise therapeutically active or nutritious plant extracts, which are known for being bad-tasting. These new solid formulation are neutral in taste. Furthermore the present invention relate to these solid formulations as well as to their use in the production of food, feed, nutritional supplement and personal care products.

9 Claims, No Drawings

PROCESS OF PRODUCTION OF A FORMULATION COMPRISING THERAPEUTICALLY ACTIVE OR NUTRITIOUS PLANT EXTRACTS

CROSS-REFERENCE TO RELATED APPLICATIONS

This application is the U.S. national phase of International Application No. PCT/EP2016/071320 filed 9 Sep. 2016, which designated the U.S. and claims priority to EP Patent Application No. 15184393.5 filed 9 Sep. 2015, the entire contents of each of which are hereby incorporated by reference.

FIELD

This invention relates to a process for producing solid formulations. These solid formulations comprise therapeutically active or nutritious plant extracts, which are known for being bad-tasting. These new solid formulation are neutral in taste. Furthermore the present invention relate to these solid formulations as well as to their use in the production of food, feed, nutritional supplement and personal care products.

BACKGROUND AND SUMMARY

Therapeutically active or nutritious plant extracts are important and some of them even essential for a good and healthy diet (for humans as well as for animals). It is known to formulate such plant extracts into various forms.

By the term "therapeutically active or nutritious plant extracts" we mean that the plant extracts have a positive effect (on humans and/or animals) when administered orally or externally.

The plant extract can be from any part of a plant, such as from the roots, the leaves, the rods, the berries etc.

The plant extracts can be obtained by commonly known processes. Such processes can be chemical and/or physical. The extract can be obtained by chemical extraction (for example from the roots or leaves) or it can be the juice of a berries (squeezed), which is then dried.

The problem which occurs with the solid formulation of such plant extracts is that they need to protected against decomposition (so that the content of the plant extract is stable for a reasonable amount of time), but also some of the therapeutically active or nutritious plant extracts do taste awful or very strong (especially for human beings). The storage stability as well as the taste issue is a problem when the plant extract is formulated into a composition, which is used (or consumed) by a costumer. A solid formulation, which is "taste-free" can be applied better in consumer products.

A preferred plant extract is from acerola. Acerola (*Malpighia punicifolia*) is a fruit-bearing shrub or small tree, which is usually native in South America, Mexico and Central America. The extract is obtained from the berries of the plant.

An important problem is that some of the therapeutically active or nutritious plant extracts taste (when taken orally) awful.

Therefore, there is a need for improved solid formulation, wherein the therapeutically active or nutritious plant extracts do not interact significantly with sensitive ingredients in food, feed, nutritional supplement or personal care application as well as when added to an end-market product does not taste awful for the consumer.

Surprisingly, we found a way to produce such solid formulations which are able to avoid the above mentioned disadvantages.

The present invention relates to a process for the production of a solid formulation wherein the solid formulation comprising at least one therapeutically active or nutritious plant extract and at least one lipophilic material (especially glycerol monostearate, which IUPAC name is 2,3-Dihydroxypropyl octadecanoate).

DETAILED DESCRIPTION

The present invention is directed toward a solid formulation and a process (P) for the production of such solid formulation, wherein the solid formulation comprises:
(i) 20-40, weight-% (wt-%), based on the total weight of the solid formulation, of least one therapeutically active or nutritious plant extract, and
(ii) 60-80 wt-%, based on the total weight of the solid formulation, of at least one lipophilic material, characterized in that
(a) at least one therapeutically active or nutritious plant extract is suspended in the at least one liquid lipophilic material, and
(b) this suspension is atomized into a spray tower, wherein the air has such a temperature that the lipophilic material solidifies.

The new and improved solid formulation has also the additional advantages that the solid formulation is easy to produce (conventional spray technology), the solid formulation has excellent properties to mask sour/bitter tastes, the solid formulation is a non-sticky powder, and the therapeutically active or nutritious plant extract is very well protected against moisture.

The therapeutically active or nutritious plant extract is preferably an Acerola plant extract.

In a preferred embodiment, the amount of this plant extract is 20-35 wt-%, based on the total weight of the solid formulation.

Therefore, the present invention also relates to a process (P1), which is process (P), wherein the therapeutically active or nutritious plant extract is an Acerola plant extract.

In a preferred embodiment, the amount of the therapeutically active or nutritious plant extract in the solid formulation is 20-35 wt-%, based on the total weight of the solid formulation.

Therefore the present invention also relates to a process (P2), which is process (P) or (P1), wherein the amount of the therapeutically active or nutritious plant in the solid formulation is 20-35 wt-%, based on the total weight of the solid formulation.

In a preferred embodiment, the amount of the lipophilic material in the solid formulation is 65-80 wt-%, based on the total weight of the solid formulation.

Therefore the present invention also relates to a process (P3), which is process (P), (P1) or (P2), wherein the lipophilic material in the solid formulation is 65-80 wt-%, based on the total weight of the solid formulation.

Lipophilic material in the context of the present invention can be waxes as well as fats.

Waxes in the context of the present invention are organic compounds that characteristically consist of a long alkyl chains. Natural waxes (plant, animal) are typically esters of fatty acids and long chain alcohols. Synthetic waxes are long-chain hydrocarbons lacking functional groups.

Fats, which are used for the embodiments of the present invention, consist of a wide group of compounds that are generally soluble in organic solvents and largely insoluble in water.

Hydrogenated fats (or saturated fats) in the context of the present invention are generally triesters of glycerol and fatty acids. Fatty acids are chains of carbon and hydrogen atoms, with a carboxylic acid group at one end. Such fats can have natural or synthetic origin. It is possible to hydrogenate a (poly)unsaturated fat to obtain a hydrogenated (saturated) fat.

Especially suitable waxes and fats have a drop point of from 30 to 90° C., preferably 40 to 80° C. Waxes in the context of the present invention are organic compounds that characteristically consist of a long alkyl chains. Natural waxes (plant, animal) are typically esters of fatty acids and long chain alcohols. Synthetic waxes are long-chain hydrocarbons lacking functional groups.

The drop point of a material is that temperature (in ° C.) when the material begins to melt under standardized conditions. The material is heated so long until it changes the state of matter from solid to liquid. The drop point is the temperature when the first drop is released from the material. The determination of the drop point (Tropfpunkt) is carried out as described in the standard norm DIN ISO 2176.

Preferred examples of waxes and fats suitable for the present invention are glycerol monostearate, carnauba wax, candelilla wax, palmitic acid, stearic acid hydrogenated cottonseed oil and hydrogenated rapeseed oil. These compounds can be used as such or as mixtures.

Therefore the present invention also relates to a process (P4), which is process (P), (P1), (P2) or (P3), wherein the lipophilic material are waxes and fats having a drop point of from 30 to 90° C., preferably 40 to 80° C.

Therefore the present invention also relates to a process (P4'), which is process (P4), wherein the lipophilic material are waxes and fats chosen from the group consisting of glycerol monostearate, carnauba wax, candelilla wax, palmitic acid, stearic acid hydrogenated cottonseed oil and hydrogenated rapeseed oil. These compounds can be used as such or as mixtures.

Therefore the present invention also relates to a process (P4"), which is process (P4) or (P4'), wherein the lipophilic material is glycerol monostearate.

It is clear that the lipophilic material, which are not in a liquid state need to be molten before used in the process according to the present invention.

Therefore the present invention also relates to a process (P5), which is process (P), (P1), (P2), (P3), (P4), (P4') or (P4"), wherein the lipophilic material, which is solid at room temperature is molten before used in the process.

To melt the lipophilic material usually a temperature of above 30° C. is chosen. The temperature is depending on the melting or drop point of lipophilic material. A usual and also preferred range is between 50° C. and 100° C. (more preferably 60° C. 100° C.).

Therefore the present invention also relates to a process (P5'), which is process (P5), wherein the lipophilic material, which is solid at room temperature is heated up to a temperature of above 30° C. before used in the process.

Therefore the present invention also relates to a process (P5"), which is process (P5), wherein the lipophilic material, which is solid at room temperature is heated up to a temperature of between 50° C. and 100° C. (more preferably between 60° C. and 100° C.).

Therefore the present invention also relates to a process (P5'''), which is process (P5), wherein the lipophilic material, which is solid at room temperature is heated up to a temperature of between 60° C. and 100° C.

The average particle sizes (d50) of the particles of the solid formulation obtained by any of the process (P), (P1), (P2), (P3), (P4), (P4'), (P4"), (P5), (P5'), (P5") and/or (P5''') is usually between 40-500 μm. The average particle sizes (d50) is measured by a MALVERN MasterSizer3000 (for all values of the present patent application).

The therapeutically active or nutritious plant extract is usually and preferably suspended in the liquid lipophilic material under stirring.

In step (b) of the process according to the present invention, the suspension (formed from the least one therapeutically active or nutritious plant extract and the least one lipophilic material) is atomized into a spray tower, wherein the air (inside the spray tower) has such a temperature that the lipophilic material solidifies.

This temperature is usually below 50° C., preferably below 40°. (Usually a range of −10° to 50° C., preferably −10° to 40° C.).

Therefore the present invention also relates to a process (P6), which is process (P), (P1), (P2), (P3), (P4), (P4'), (P4"), (P5), (P5'), (P5") or (P5'''), wherein the suspension is atomized into a spray tower, wherein the air has s temperature of below 50° C.

Therefore the present invention also relates to a process (P6'), which is process (P), (P1), (P2), (P3), (P4), (P4'), (P4"), (P5), (P5'), (P5") or (P5'''), wherein the suspension is atomized into a spray tower, wherein the air has a temperature of below 40° C.

Therefore the present invention also relates to a process (P6"), which is process (P), (P1), (P2), (P3), (P4), (P4'), (P4"), (P5), (P5'), (P5") or (P5'''), wherein the suspension is atomized into a spray tower, wherein the air has a temperature of −10° to 50° C.

Therefore the present invention also relates to a process (P6'''), which is process (P), (P1), (P2), (P3), (P4), (P4'), (P4"), (P5), (P5'), (P5") or (P5'''), wherein the suspension is atomized into a spray tower, wherein the air has a temperature of −10° to 40° C.

The solid formulation according to the present invention can also comprise other ingredients, which can be useful for the solid formulation, for the production of the solid formulation and/or the use of the solid formulation.

These other ingredients can be added at any stage to the process according to the present invention. This means they can be added to the therapeutically active or nutritious plant extract and/or to the lipophilic material and/or to the suspension. Optionally also some auxiliary compound can be used in the spray drying process.

Furthermore the present invention relates to a process wherein the solid formulation consists of
(i) 20-40, weight-% (wt-%), based on the total weight of the solid formulation, of least one therapeutically active or nutritious plant extract, and
(ii) 60-80 wt-%, based on the total weight of the solid formulation, of glycerol monostearate.

Therefore the present invention also relates to a process (P7), which is process (P), (P1), (P2), (P3), (P4), (P4'), (P4"), (P5), (P5'), (P5"), (P5'''), (P6), (P6'), (P6") or (P6'), wherein the solid formulation consists of
(i) 20-40, weight-% (wt-%), based on the total weight of the solid formulation, of least one therapeutically active or nutritious plant extract, and
(ii) 60-80 wt-%, based on the total weight of the solid formulation, of glycerol monostearate A very preferred embodiment is the following process, wherein
(a) 20-40, weight-% (wt-%), based on the total weight of the solid formulation, glycerol monostearate is molted at a temperature of between 60° C. and 100° C., and
(b) 60-80 wt-%, based on the total weight of the solid formulation, Acerola plant extract is suspended in the molten glycerol monostearate (by stirring), and then afterwards
(c) this suspension is atomized into a spray tower, wherein the air (in the spray tower) has a temperature of below 40° C.

Therefore the present invention also relates to a process (P8), wherein
(a) 20-40, weight-% (wt-%), based on the total weight of the solid formulation, glycerol monostearate is molted at a temperature of between 60° C. and 100° C., and
(b) 60-80 wt-%, based on the total weight of the solid formulation, Acerola plant extract is suspended in the molten glycerol monostearate (by stirring), and then afterwards
(c) this suspension is atomized into a spray tower, wherein the air (in the spray tower) has a temperature of below 40° C.

As stated above the solid formulation obtained by the process according to the present invention is in a powder form.

Furthermore the present invention relates to a solid formulation (F1) comprising
(i) 20-40, weight-% (wt-%), based on the total weight of the solid formulation, of least one therapeutically active or nutritious plant extract, and
(ii) 60-80 wt-%, based on the total weight of the solid formulation, of at least one lipophilic material.

The new and improved solid formulation has also the additional advantages that the solid formulation is easy to produce (conventional spray technology), the solid formulation has excellent properties to mask sour/bitter or adstringent tastes, the solid formulation is a non-sticky powder, and the one therapeutically active or nutritious plant extract is very well protected against moisture.

The therapeutically active or nutritious plant extract is preferably an Acerola plant extract.

Therefore the present invention also relates to a solid formulation (F2), which is formulation (F1), wherein the therapeutically active or nutritious plant extract is an Acerola plant extract.

In a preferred embodiment, the amount of this plant extract is 20-35 wt-%, based on the total weight of the solid formulation.

Therefore the present invention also relates to a solid formulation (F3), which is formulation (F1) or (F2), wherein the amount of the therapeutically active or nutritious plant extract is 20-35 wt-%, based on the total weight of the solid formulation.

In a preferred embodiment, the amount of the lipophilic material is 65-80 wt-%, based on the total weight of the solid formulation.

Therefore the present invention also relates to a solid formulation (F4), which is formulation (F1), (F2) or (F3), wherein the lipophilic material is 65-80 wt-%, based on the total weight of the solid formulation.

Therefore the present invention also relates to a solid formulation (F5), which is formulation (F1), (F2), (F3) or (F4), wherein the lipophilic material are waxes and fats having a drop point from 30 to 90° C., preferably 40 to 80° C.

Therefore the present invention also relates to a solid formulation (F5'), which is formulation (F5), wherein the lipophilic material are waxes and fats chosen from the group consisting of glycerol monostearate, carnauba wax, candelilla wax, palmitic acid, stearic acid hydrogenated cottonseed oil and hydrogenated rapeseed oil. These compounds can be used as such or as mixtures.

Therefore the present invention relates to a solid formulation (F5"), which is formulation (F5) or (F5'), wherein the lipophilic material is glycerol monostearate.

Therefore the present invention also relates to a solid formulation (F6), which is formulation (F1), (F2), (F3), (F4) or (F5), wherein the average particle sizes (d50) of the particles of the solid formulation according to the present invention is between 40-500 μm.

Therefore the present invention also relates to a solid formulation (F7), which consists of
(i) 20-40, weight-% (wt-%), based on the total weight of the solid formulation, of least one therapeutically active or nutritious plant extract, and
(ii) 60-80 wt-%, based on the total weight of the solid formulation, of glycerol monostearate.

Therefore the present invention also relates to a solid formulation (F7), which consists of
(i) 20-40, weight-% (wt-%), based on the total weight of the solid formulation, of an Acerola plant extract, and
(ii) 60-80 wt-%, based on the total weight of the solid formulation, of glycerol monostearate.

The solid formulations (F1), (F2), (F3), (F4), (F5), (F6), (F6'), (F6"), (F7) and (F8) according to the present invention can be used as such or it can be used in any other compositions.

The solid formulations (F1), (F2), (F3), (F4), (F5), (F6), (F6'), (F6"), (F7) and (F8) as such or preferably the formulations (F1), (F2), (F3), (F4), (F5), (F6), (F6'), (F6"), (F7) and (F8) incorporated into another composition can be used as food, feed, nutritional supplement and/or personal care products.

Preferred is the use of at least one solid formulation (F1), (F2), (F3), (F4), (F5), (F6), (F6'), (F6"), (F7) and (F8) in the production of food and/or feed compositions.

The amount of the solid formulation (F1), (F2), (F3), (F4), (F5), (F6), (F6'), (F6"), (F7) and/or (F8), in the final consumer product, depends on the application and the consumer demand.

Furthermore the present invention relates to food, feed, nutritional supplement and/or personal care products comprising at least one solid formulation (F1), (F2), (F3), (F4), (F5), (F6), (F6'), (F6"), (F7) and (F8).

These products can be in any commonly known and used form.

The following examples serve to illustrate the invention.

EXAMPLES

Example 1: Acerola 33%

Melt 16.00 kg Glycerol Monostearate in a stirred vessel at 65-85° C.

Suspend 8.00 kg Acerola Powder 20% Vitamin C into the molten Glycerol Monostearate by normal stirring until a homogeneous suspension is made (app. 20-40 min). Maintain 65-85° C. product temperature.

Feed the suspension to a spray tower were an atomizer will generate droplets of a suitable size out of the suspension. The spray tower has to be operated at an air temperatures of 25° C. to solidify the atomized droplets of the suspension.

Collect the solidified product (powder).

The invention claimed is:

1. A process for the production of a solid formulation comprising:
   (i) 20-40 weight-% (wt-%), based on the total weight of the solid formulation, of an Acerola plant extract, and
   (ii) 60-80 wt-%, based on the total weight of the solid formulation, of at least one lipophilic material, wherein the process comprises the steps of:
   (a) providing the lipophilic material in a molten state,
   (b) forming a suspension of the lipophilic material and the Acerola plant extract by suspending the Acerola plant extract in the molten lipophilic material, and thereafter
   (c) introducing the suspension into a spray tower comprising atomizing air, in which the atomizing air has a temperature that causes solidification of the liquid lipophilic material, thereby forming solid particles thereof containing the Acerola plant extract.

2. The process according to claim 1, wherein the lipophilic material is at least one wax and/or fat having a drop point of from 30 to 90° C.

3. The process according to claim 1, wherein the lipophilic material is at least one wax and/or fat selected from the group consisting of glycerol monostearate, carnauba wax, candelilla wax, palmitic acid, stearic acid hydrogenated cottonseed oil and hydrogenated rapeseed oil.

4. The process according to claim 1, wherein the lipophilic material is glycerol monostearate.

5. The process according to claim 1, wherein the suspension formed according to step (b) comprises 20-35 wt-%, based on the total weight of the solid formulation, of the Acerola plant extract.

6. The process according to claim 1, wherein the suspension formed according to step (b) comprises 65-80 wt-%, based on the total weight of the solid formulation, of the at least one lipophilic material.

7. The process according to claim 1, wherein the solid particles formed according to step (c) have an average particle size (d50) of between 40-500 μm.

8. The process according to claim 1, wherein the solid formulation consists of:
   (i) 20-40 weight-% (wt-%), based on the total weight of the solid formulation, of the Acerola plant extract, and
   (ii) 60-80 wt-%, based on the total weight of the solid formulation, of glycerol monostearate as the lipophilic material.

9. The process according to claim 2, wherein the at least one wax and/or fat has a drop point of from 40 to 80° C.

* * * * *